US010383342B2

(12) United States Patent
Farmer et al.

(10) Patent No.: US 10,383,342 B2
(45) Date of Patent: Aug. 20, 2019

(54) BAKED GOODS

(75) Inventors: Sean Farmer, Miami Beach, FL (US); Andrew R. Lefkowitz, University Heights, OH (US); Michael Bush, Brecksville, OH (US); David Maske, Chagrin Falls, OH (US)

(73) Assignee: Ganeden Biotech, Inc., Mayfield Heights, OH (US)

(*) Notice: Subject to any disclaimer, the term of this patent is extended or adjusted under 35 U.S.C. 154(b) by 0 days.

(21) Appl. No.: 12/229,862

(22) Filed: Aug. 27, 2008

(65) Prior Publication Data

US 2009/0186126 A1 Jul. 23, 2009

Related U.S. Application Data

(60) Provisional application No. 60/966,897, filed on Aug. 29, 2007.

(51) Int. Cl.
| | | |
|---|---|---|
| *A21D 8/04* | (2006.01) | |
| *C12R 1/07* | (2006.01) | |
| *A23P 10/30* | (2016.01) | |
| *A23L 7/104* | (2016.01) | |
| *A23L 7/13* | (2016.01) | |
| *A23L 19/18* | (2016.01) | |
| *A23L 33/135* | (2016.01) | |

(52) U.S. Cl.
CPC .............. *A21D 8/045* (2013.01); *A21D 8/04* (2013.01); *A23L 7/104* (2016.08); *A23L 7/13* (2016.08); *A23L 19/18* (2016.08); *A23L 33/135* (2016.08); *A23P 10/30* (2016.08); *C12R 1/07* (2013.01); *A23V 2002/00* (2013.01)

(58) Field of Classification Search
CPC ....................................................... A23L 1/30
USPC ......................................................... 426/61
See application file for complete search history.

(56) References Cited

U.S. PATENT DOCUMENTS

| | | | |
|---|---|---|---|
| 3,091,572 A | 5/1963 | Luedemann et al. | |
| 3,840,684 A | 10/1974 | Fazzina et al. | |
| 4,110,477 A | 8/1978 | Naruse et al. | 426/46 |
| 4,144,346 A | 3/1979 | Heeres et al. | |
| 4,278,690 A | 7/1981 | Onodera | |
| 4,321,258 A | 3/1982 | Dunlap | |
| 4,323,651 A | 4/1982 | Long et al. | 435/207 |
| 4,695,546 A | 9/1987 | Aiba et al. | |
| 4,756,913 A | 7/1988 | Khorkova et al. | |
| 4,956,177 A | 9/1990 | King et al. | |
| 4,980,180 A | 12/1990 | Cully et al. | 426/47 |
| 5,021,344 A | 6/1991 | Armau et al. | |
| 5,079,164 A | 1/1992 | Kirkovits et al. | 435/252.5 |
| 5,102,800 A | 4/1992 | Hirikoshi | 435/193 |
| 5,176,911 A | 1/1993 | Tosi et al. | |
| 5,200,336 A | 4/1993 | Kong et al. | 435/199 |
| 5,266,315 A | 11/1993 | Taguchi et al. | |
| 5,413,960 A | 5/1995 | Dobrogosz et al. | |
| 5,439,678 A | 8/1995 | Dobrogosz et al. | |
| 5,439,995 A | 8/1995 | Bailly et al. | |
| 5,531,998 A | 7/1996 | Mares et al. | |
| 5,534,253 A | 7/1996 | Casas et al. | |
| 5,665,354 A | 9/1997 | Neyra et al. | |
| 5,785,990 A | 7/1998 | Langrehr | |
| 5,814,319 A | 9/1998 | Nakano | |
| 5,895,672 A | 4/1999 | Cooper | |
| 5,968,569 A * | 10/1999 | Cavadini | A61K 35/742 426/61 |
| 6,080,401 A | 6/2000 | Reddy et al. | |
| 6,132,710 A | 10/2000 | Panigrahi et al. | |
| 6,461,607 B1 * | 10/2002 | Farmer | 424/93.45 |
| 6,531,126 B2 | 3/2003 | Farmer | |
| 6,537,543 B1 | 3/2003 | Minakawa | |
| 6,645,506 B1 | 11/2003 | Farmer | |
| 6,706,290 B1 | 3/2004 | Kajander et al. | |
| 6,716,435 B1 | 4/2004 | Farmer et al. | |
| 6,723,326 B1 | 4/2004 | Farmer | |
| 6,733,751 B2 | 5/2004 | Farmer | |
| 6,811,786 B1 | 11/2004 | Farmer et al. | |
| 6,835,397 B2 * | 12/2004 | Lee et al. | 424/461 |
| 6,849,256 B1 | 2/2005 | Farmer | 424/93.46 |
| 6,905,692 B2 | 6/2005 | Farmer | |
| 7,024,497 B1 | 4/2006 | Maffezoni | |
| 7,025,974 B2 | 4/2006 | Farmer et al. | |
| 7,048,950 B2 | 5/2006 | Farmer | |
| 7,232,571 B2 | 6/2007 | Farmer et al. | |
| 7,371,407 B2 | 5/2008 | Farmer | |
| 7,374,753 B1 | 5/2008 | Farmer et al. | |
| 7,507,402 B1 | 3/2009 | Farmer et al. | |
| 7,541,042 B2 | 6/2009 | Farmer | |
| 7,544,363 B2 | 6/2009 | Farmer | |

(Continued)

FOREIGN PATENT DOCUMENTS

| | | | |
|---|---|---|---|
| CA | 2606495 A1 | 11/2006 | |
| CN | 1507812 A | 6/2004 | |

(Continued)

OTHER PUBLICATIONS

Rogers, R. F. 1978. Bacillus isolates from refrigerated doughs, wheat flour and wheat. Cereal Chem. 55:671-674.*
JP 2001-292763-Machine Translation.*
JP-1998-084845-Machine Translation.*
Amaha, M. et al. 1955. Sporulation requirements of *Bacillus coagulans* var. *thermoacidurans* in complex media. J. Bacteriol. 72:34-41.*

(Continued)

*Primary Examiner* — Hamid R Badr

(74) *Attorney, Agent, or Firm* — Mintz Levin Cohn Ferris Glovsky and Popeo, P.C.; Ingrid A. Beattie; Nicholas A. Zachariades

(57) ABSTRACT

The present invention describes compositions and methods comprising lactic acid-producing bacteria in baked goods.

11 Claims, No Drawings

(56) References Cited

U.S. PATENT DOCUMENTS

| | | |
|---|---|---|
| 7,555,715 B2 | 6/2009 | Randall et al. |
| 7,700,093 B2 | 4/2010 | Farmer et al. |
| 7,708,988 B2 | 5/2010 | Farmer |
| 7,713,726 B2 | 5/2010 | Farmer |
| 7,767,203 B2 | 8/2010 | Farmer et al. |
| 7,807,151 B2 | 10/2010 | Farmer |
| 7,807,185 B2 | 10/2010 | Farmer |
| 7,854,927 B2 | 12/2010 | Farmer et al. |
| 8,097,247 B2 | 1/2012 | Farmer |
| 8,187,590 B2 | 5/2012 | Farmer |
| 8,273,346 B2 | 9/2012 | Farmer et al. |
| 8,277,799 B2 | 10/2012 | Farmer |
| 8,343,484 B2 | 1/2013 | Farmer et al. |
| 8,349,337 B1 | 1/2013 | Farmer et al. |
| 8,409,591 B2 | 4/2013 | Farmer et al. |
| 8,568,743 B2 | 10/2013 | Farmer et al. |
| 8,568,744 B2 | 10/2013 | Farmer et al. |
| 8,697,055 B2 | 4/2014 | Farmer |
| 8,821,854 B2 | 9/2014 | Farmer et al. |
| 9,192,659 B2 | 11/2015 | Farmer et al. |
| 9,220,736 B2 | 12/2015 | Farmer et al. |
| 9,301,982 B2 | 4/2016 | Lefkowitz |
| 9,446,111 B2 | 9/2016 | Farmer et al. |
| 9,597,286 B2 | 3/2017 | Lefkowitz |
| 9,622,502 B2 | 4/2017 | Farmer et al. |
| 9,757,442 B2 | 9/2017 | Farmer et al. |
| 2003/0031659 A1 | 2/2003 | Farmer |
| 2003/0138936 A1 | 7/2003 | Mizuguchi et al. |
| 2003/0185811 A1 | 10/2003 | Teasdale et al. |
| 2004/0010510 A1 | 1/2004 | Hotti |
| 2004/0071685 A1 | 4/2004 | Houston et al. |
| 2004/0161522 A1 | 8/2004 | Toves |
| 2004/0175459 A1 | 9/2004 | Ting |
| 2004/0197277 A1* | 10/2004 | Gonzales ............... 424/48 |
| 2005/0100535 A1* | 5/2005 | Farmer et al. ........ 424/93.46 |
| 2005/0153040 A1 | 7/2005 | Axelrod et al. |
| 2005/0154682 A1 | 7/2005 | Taylor |
| 2005/0202145 A1 | 9/2005 | Dorr et al. |
| 2005/0232909 A1 | 10/2005 | Farmer |
| 2005/0271643 A1 | 12/2005 | Sorokulova et al. |
| 2006/0099197 A1 | 5/2006 | Farmer |
| 2006/0112584 A1 | 6/2006 | Jones |
| 2006/0154350 A1 | 7/2006 | Kolbakov et al. |
| 2006/0177429 A1 | 8/2006 | Farmer et al. ........ 424/93.46 |
| 2006/0184538 A1 | 8/2006 | Randall et al. |
| 2006/0204633 A1 | 9/2006 | Moore |
| 2007/0059400 A1 | 3/2007 | Goto et al. |
| 2008/0233104 A1 | 9/2008 | Farmer |
| 2008/0274153 A1 | 11/2008 | Farmer |
| 2008/0305096 A1 | 12/2008 | Verdegem et al. |
| 2009/0186057 A1 | 7/2009 | Farmer et al. |
| 2009/0208606 A1* | 8/2009 | Hakansson et al. ......... 426/18 |
| 2009/0232941 A1 | 9/2009 | Farmer |
| 2010/0074993 A1* | 3/2010 | Cooreman ........... A23G 9/363 |
| | | 426/61 |
| 2010/0210000 A1 | 8/2010 | Farmer et al. |
| 2011/0020305 A1 | 1/2011 | Farmer |
| 2011/0195154 A1 | 8/2011 | Farmer |
| 2011/0274676 A1 | 11/2011 | Farmer et al. |
| 2012/0251512 A1 | 10/2012 | Farmer et al. |
| 2013/0164398 A1 | 6/2013 | Farmer |
| 2013/0195824 A1 | 8/2013 | Farmer et al. |
| 2013/0216577 A1 | 8/2013 | Farmer et al. |
| 2013/0251695 A1 | 9/2013 | Farmer et al. |
| 2013/0344046 A1 | 12/2013 | Farmer et al. |
| 2014/0242051 A1 | 8/2014 | Farmer |
| 2015/0044317 A1 | 2/2015 | Farmer et al. |
| 2015/0313951 A1 | 11/2015 | Cash et al. |
| 2016/0213612 A1 | 7/2016 | Lefkowitz |
| 2016/0213613 A1 | 7/2016 | Lefkowitz |
| 2016/0213614 A1 | 7/2016 | Lefkowitz |
| 2016/0213615 A1 | 7/2016 | Lefkowitz |
| 2017/0000872 A1 | 1/2017 | Farmer et al. |
| 2017/0035813 A1 | 2/2017 | Farmer et al. |
| 2017/0189331 A1 | 7/2017 | Lefkowitz |
| 2017/0189457 A1 | 7/2017 | Farmer et al. |
| 2017/0280755 A1 | 10/2017 | Farmer et al. |

FOREIGN PATENT DOCUMENTS

| | | | |
|---|---|---|---|
| DE | 4132296 C1 | 12/1992 | |
| EP | 1020123 A1 | 7/2000 | |
| EP | 1344458 A1 | 9/2003 | |
| EP | 1810579 A1 | 7/2007 | |
| GB | 1040278 A | 8/1966 | |
| JP | S45032905 | 10/1970 | |
| JP | S52136998 A | 11/1977 | |
| JP | S5350399 A | 5/1978 | |
| JP | 64083025 | 3/1989 | |
| JP | 4082827 A | 3/1992 | |
| JP | 4158771 A | 6/1992 | |
| JP | 6166626 A | 6/1994 | |
| JP | 08175921 | 7/1996 | |
| JP | H09107869 | 4/1997 | |
| JP | H1084845 A | 4/1998 | |
| JP | H10084845 | 4/1998 | |
| JP | 11169145 A | 6/1999 | |
| JP | 11335285 A | 12/1999 | |
| JP | 2000093162 A | 4/2000 | |
| JP | 2001252012 A | 9/2001 | |
| JP | 2001-292763 | * 10/2001 | ............ C12N 1/20 |
| JP | 2001286278 A | 10/2001 | |
| JP | 2002502430 A | 1/2002 | |
| JP | 2002-522393 A | 7/2002 | |
| JP | 2003513649 A | 4/2003 | |
| JP | 2004337125 A | 12/2004 | |
| JP | 2005137357 A | 6/2005 | |
| JP | 2005536994 A | 12/2005 | |
| JP | 2006025621 A | 2/2006 | |
| JP | 2006254837 A | 9/2006 | |
| JP | 2007000140 A | 1/2007 | |
| JP | 2007044014 A | 2/2007 | |
| JP | 2007054081 A | 3/2007 | |
| JP | 2007082403 A | 4/2007 | |
| JP | 2007537270 A | 12/2007 | |
| JP | 2008013543 A | 1/2008 | |
| TW | 228974 B | 3/2005 | |
| WO | WO-8905849 A1 | 6/1989 | |
| WO | WO-9314187 A1 | 7/1993 | |
| WO | WO 94/00019 | * 1/1994 | ............ A21D 15/00 |
| WO | WO-9400019 A1 | 1/1994 | |
| WO | WO-9411492 A1 | 5/1994 | |
| WO | WO-9611014 A1 | 4/1996 | |
| WO | WO-9729762 A1 | 8/1997 | |
| WO | WO-9734615 A1 | 9/1997 | |
| WO | WO-9854982 A1 | 12/1998 | |
| WO | WO-0007606 A2 | 2/2000 | |
| WO | WO-0134168 A1 | 5/2001 | |
| WO | WO-04004747 A1 | 1/2004 | |
| WO | WO-04008870 A1 | 1/2004 | |
| WO | WO-2005019417 A2 | 3/2005 | |
| WO | WO-2005055934 A2 | 6/2005 | |
| WO | WO-05092122 A1 | 10/2005 | |
| WO | WO-05110445 A2 | 11/2005 | |
| WO | WO-2005117926 A1 | 12/2005 | |
| WO | WO-2006007470 A1 | 1/2006 | |
| WO | WO-2006/090729 A1 | 8/2006 | |
| WO | WO-2007012847 A1 | 2/2007 | |
| WO | WO-2007/058027 A1 | 5/2007 | |
| WO | WO-08112296 A1 | 9/2008 | |
| WO | WO-09029267 A1 | 3/2009 | |
| WO | WO-09051753 A1 | 4/2009 | |

OTHER PUBLICATIONS

Christi et al., "Role of dietary sulphate in the regulation of methanogenesis in the human large intestine", *Gut*, 33:1234-1238 (1992).

Gibson et al., Selective stimulation of bifidobacteria in the human colon by oligofructose and inulin, *Gastroenterol.*, 108:975-982 (1995).

(56) References Cited

OTHER PUBLICATIONS

Nakamura et al., "Taxonomic study of *Bacillus coagulans* Hammer 1915 with a proposal for *Bacillus smithii* sp. Nov.", *Int'l. J. Syst. Bacterial.*, 38(1):63-73 (1988).
ATCC Catalogue of Bacteria and Bacteriophages, Accession No. 31284.
*Bergey's Manual of Systematic Bacteriology*, vol. 2, Sneath et al., eds., Williams & Wilkens, Baltimore, MD, p. 1117 (1986).
Database WPI Week 198532 Thomson Scientific, London, GB; AN 1985-195034 XP002502608 & SU 1 134 151 A (Kiev Food Ind Techn Inst) (Jan. 15, 1985).
Balasubramaniam et al."High-Pressure Food Processing", Food Sci Tech Int: 14(5):413-418 (2008).
Balasubramaniam et al., "Principles and Application of High Pressure-Based Technologies in the Food Industry", Ann. Rev. Food Sci Technol. 6:435-62.
Daryaei. et al. "Kinetics of Bacillus coagulans spore inactivation in tomato juice by combined pressure-heat treatment" Food Control 30:168-75( 2013).
Johnson et al."Inactivation of Bacillus coagulans Spores by Pressure-assisted Thermal Processing", Oculus, vol. 1: 35-38 (2010).
Lino et al. "A Study on the Effect of Bacillus Coagulans, a Spore-Forming Lactic Acid Bacteria, in Improving the Properties of Feces." *Prog. Med.* 17(1997):3299-3302. (No English Translation Available).
Maruzen Shokuhin Sogo Jiten. Maruzen General Encyclopedia of Food. Mar. 25, 1998. p. 861.
Maruzen Shokuhin Sogo Jiten. Maruzen General Encyclopedia of Food. Mar. 25, 1998. p. 999.
Peng et al. "Thermal Inactivation Kinetics of Bacillus coagulans Spores in Tomato Juice", Journal of food protection, vol. 75, No. 7; 1236-1242 (2012).
Rice et al. "Boiling and Bacillus Spores" Emerg Infect Dis. Oct. 2004; 10(10): 18871888 (available at www.ncbi.nlm.nih.gov/pmc/articles/PMC3323245/table/T1l).
Schiffrin et al. "Immune Modulation of Blood Leukocytes in Humans by Lactic Acid Bacteria: Criteria for Strain Selection." *Am. J. Clin. Nutr.* 66(1997):515S-520S.
Sekine et al. "Induction and Activation of Tumoricidal Cells In Vivo and In Vitro by the Bacterial Cell Wall of *Bifdobacterium infantis*" Bifidobact Microflora. 13.2(1994):65-77.
Shannon and French. "Multiple-Antibiotic-Resistant *Salmonella*." *Lancet*. 352(1998):490.
Shoenfeld et al. "Guillain-Barre as an Autoimmune Disease." *Int. Arch. Allergy Immunot* 109(1996):318-326.
Smith et al. "Fluoroquinolone-Resistant *Campylobacter* Isolated from Humans and Poultry in Minnesota." *Int. Conf. Emerging Infect. Dis.* 1998:69.
Solis-Pereyra et al. "Induction of Human Cytokines by Bacteria Used in Dairy Foods." *Nutr. Res.* 13(1993):1127-1140.
Sorvillo et al. "Incidence of Campylobacteriosis Among Patients with AIDS in Los Angeles County." *J. Acquired Immune Defic. Syndr.* 4(1991):598-602.
Standiford et al. "Lipoteichoic Acid Induces Secretion of Interleukin-8 From Human Blood Monocytes: A Cellular and Molecular Analysis." *Infect. Immun.* 62.1(1994):119-125.
Sussman et al. "Clinical Manifestations and Therapy of Lactobacillus Endocarditis: Report of a Case and Review of the Literature." *Rev Infect. Dis.* 8.5(1986):771-776.
Suzuki et al. "Purification and Characterization of *Bacillus coagulans* Oligo-1,6-Glucosidase." *Eur. J. Biochem.* 158.1(1986):77-83.
Tauxe. "Epidemiology of *Campylobacter jejuni* Infections in the United States and Other Industrial Nations." *Campylobacter jejuni* Current Status and Future Trends. Nachamkin et al., eds. Washington, DC:American Society for Microbiology. (1992):9-19.
The Merck Index. Rahway, NJ: Merck & Co., Inc. Windholz et al., eds. 10(1983):549.
Thomason et al. "Bacterial Vaginosis: Current Review With Indications for Asymptomatic Therapy." *Am. J. Obstet Gynecol.* 165(1991):1210-1217.

Tojo et al. "The Effects of *Bifidobacterium breve* Administration on Campylobacter Enteritis." *Acta Paediatr. Jpn.* 29(1987):160-167.
Wang et al. "Inactivation Kinetics and Reduction of Bacillus Coagulans Spore by the Combination of High Pressure and Moderate Heat", Journal of Food Process Engineering 32 692-708 (2009).
Winberg et al. "Pathogenesis of Urinary Tract Infection-Experimental Studies of Vaginal Resistance to Colonization." *Pediatr. Nephrol.* (1993):509-514.
Zimmermann et al."Modeling the inactivation kinetics of Bacillus coagulans spores in tomato pulp from the combined effect of high pressure and moderate temperature", LWT Food Sci and Tech, (53):107-112 (2013).
Hammer, 1915, Bacteriological Studies on the Coagulation of Evaporated Milk, Iowa Agric. Expt. Sta. Res. Bull. 19:119-132.
Pepe et al., 2003, Rope-Producing Strains of *Bacillus* spp. from Wheat Bread and Strategy for Their Control by Lactic Acid Bacteria, Applied and Environmental Microbiology 69(4):2321-29.
Cornelis et al., 1982, Cloning and expression of a Bacillus coagulans amylase gene in *Escherichia coli*, Mol Gen Genet. 186(4):507-11 [Abstract].
Akoachere et al., Antibacterial effect of Zingiber officinale and Garcinia kola on respiratory tract pathogens. East Afr Med J. Nov. 2002;79(11):588-92.
Al-Turki, A. Antibacterial effect of thyme, peppermint, sage, black pepper and garlic hydrosols against Bacillus subtilis and *Salmonella enteritidis*. Journal of Food, Agriculture & Environment. 2007;5(2):92-4.
Barrile et al., Microflora of cocoa beans before and after roasting at 150 C. J Milk Food Technol. 1971;34(7):369-71.
Ekwenye et al., Antibacterial Activity of Ginger (*Zingiber officinale*) Roscoe and Garlic (*Allium sativum* L.) Extracts on *Escherichia coli* and *Salmonella typhi*. International Journal of Molecular Medicine and Advance Science. 2005;1(4):411-6.
Hattori et al., Studies on Dental Caries Prevention by Traditional Medicines (IX) Potent Antibacterial Action of Coumarin Derivatives from Licorice Roots against *Streptococcus* mutans. Shoyakugaku Zasshi. 1986;40(4):406-12.
Nanasombat et al., Antibacterial activity of crude ethanolic extracts and essential oils of spices against *salmonellae* and other enterobacteria. KMITL Sci. Tech. J. Dec. 2005;5(3):527-38.
Olaleye, M. Cytotoxicity and antibacterial activity of Methanolic extract of Hibiscus sabdariffa. Journal of Medicinal Plants Research. Aug. 2007;1(1):9-13.
Pattnaik et al., Antibacterial and antifungal activity of ten essential oils in vitro. Microbios. 1996;86(349):237-46. [Abstract].
Sharaf et al., Further Study on the Antibacterial Effect of H. sabdariffa. Path Microbiol. 1996;29:120-5.
Tadhani et al., In Vitro Antimicrobial Activity of Stevia Rebaudiana Bertoni Leaves. Tropical Journal of Pharmaceutical Research. Jun. 2006;5(1):557-60.
Tanaka et al., Antibacterial Compounds of Licorice against Upper Airway Respiratory Tract Pathogens. J Nutr Sci Vitaminol. 2001;47:270-3.
Britannica.com Definition of "Leavening Agent" Accessed on Oct. 26, 2017.
Online Merriam-Webster Definition of "Muffin" Accessed on Oct. 17, 2017.
Online Merriam-Webster Definition of "Quick Bread" Accessed on Oct. 17, 2017.
Online Vocabulary.com Definition of "Muffin" Accessed on Oct. 17, 2017.
Allos. "Association Between *Campylobacter* Infection and Guillain-Barré Syndrome." *J. Infect. Dis.* 176(1997):S125-S128.
Baker et al. "Growth Requirements of 94 Strains of Thermophilic Bacilli." *Can. J. Microbiol.* 6(1960):557-563.
Barefoot et al. "Antibiosis Revisited: Bacteriocins Produced by Dairy Starter Cultures." *J. Diary Sci.* 76(1993):2366-2379.
Bernet et al. "Adhesion of Human Bifidobacterial Strains to Cultured Human Intestinal Epithelial Cells and Inhibition of Enteropathogen-Cell Interactions." *Appl. Environ. Microbiol.* 59.12(1993): 4121-4128.

(56) References Cited

OTHER PUBLICATIONS

Bernet et al. "*Lactobacillus acidophilus* LA 1 Binds to Cultured Human Intestinal Cell Lines and Inhibits Cell Attachment and Cell Invasion by Enterovirulent Bacteria." *Gut.* 35(1994):483-489.
Black et al. "Experimental *Camplylobacter jejuni* Infection in Humans." *J. Infect. Dis.* 157.3(1988):472-479.
Blaser et al. "The Influence of Immunity on Raw Milk-Associated *Campylobacter* Infection." *JAMA.* 257.1(1987):43-46.
Blaser. "Campylobacter Species." *Principles and Practice of Infectious Diseases.* Mandell et al., eds. New York: Churchill Livingstone Inc. 3(1990):1649-1658.
Challa et al. "*Bifidobacterium longum* and Lactulose Suppress Azoxymethane-Induced Colonic Aberrant Crypt foci in Rats." *Carcinogenesis.* 18.3(1997):517-521.
Cometta et al. "*Escherichia coli* Resistant to Fluoroquinolones in Patients with Cancer and Neutropenia." *New Engl. J. Med.* 330. 17(1994):1240-1241.
De Simone et al. "Effect of *Bifidobacterium bifidum* and *Lactobacillus acidophilus* on Gut Mucosa and Peripheral Blood B Lymphocytes." *Immunopharmacol. ImmunotoxicoL* 14.1&2(1992):331-340.
De Veechi et al. "*Lactobacillus sporogenes* or *Bacillus coagulans*: Misidentification or Mislabeling." *Int. J. Probiotics Prebiotics.* 1.1(2006):3-10.
El-Baz. "Herbal and Floral Teas, Infusions, or Tisanes?" *The Essence of Herbal and Floral Teas.* New York: iUniverse. (2006):1-5.
Elmer et al. "Biotherapeutic Agents. A Neglected Modality for the Treatment and Prevention of Selected Intestinal and Vaginal Infections." *JAMA.* 275.11(1996):870-876.
Famularo et al. "Stimulation of Immunity by Probiotics." *Probiotics 2: Applications and Practical Aspects.* Fuller, ed. London: Boundary Row. (1997):133-161.
Fernandez et al. "Effect of Diatomaceous Earth as an Anthelmintic Treatment on Internal Parasites and Feedlot Performance of Beef Steers." *Animal Science* 66.3(1998): 635-641.
Fuller. "Probiotics in Man and Animals." *J. Appl. BacterioL* 66(1989):365-378.
Gandhi. "Lactobacillus Sporogenes: An Advancement in Lactobacillus Therapy." *Townsend Left. Doctors Patients.* 150(1996):108-110.
Girardin et al. "Antimicrobial Activity of Foodborne *Paenibacillus* and *Bacillus* spp. Against *Clostridium botulinum .*" *J. Food Protection.* 65.5(2002).806-813.
Gorbach. "Lactic Acid Bacteria and Human Health." *Ann. Med.* 22(1990):37-41.
Hata et al. "Meningitis Caused by *Bifidobacterium* in an Infant." *Pediatr. Infect. Dis.* 7(1988):669-671.
Hill et al. "Vaginitis: Current Microbiologic and Clinical Concepts." *Can. Med. Assoc. J.* 134(1986):321-331.
Hyronimus et al. "Coagulin, a Bacteriocin-Like Inhibitory Substance Produced by Bacillus Coagulans 14." *J. Appl. Microbiol.* 85.1(1998):42-50.
Jacobs-Reitsma et al. "The Induction of Quinolone Resistance in *Campylobacter* Bacteria in Broilers by Quinolone Treatment." *Campylobacter, Helicobacters, and Related Organisms.* Newell et al., eds. New YorkL Plenum Press. (1996):307-311.
Ketley. "Pathogenesis of Enteric Infection by *Campylobacter.*" *Microbiol.* 143(1997):5-21.
Kim et al. "Development of Lactobacillus-Sporogenes Resistant to Rifampicin an Antituberculosis Agent." *Korean J. Micro.* 27.2(1989):155-161. (English Abstract Only).
Klaenhammer. "Genetics of Bacteriocins Produced by Lactic Acid Bacteria." *FEMS Microbial. Rev.* 12(1993):39-85.
Koo et al. "Long-Term Effect of Bifidobacteria and Neosugar on Precursor Lesions of Colonic Cancer in CFI Mice." *Nutrit. Rev.* 16(1991):249-257.
Korshunov et al. "Effect of the Combined Administration of Antibiotic Resistant Bifidobacteria and the Corresponding Antibiotics on the Survival of Irradiated Mice." *Zh. MikrobioL Epidemol. ImmunobioL* 5(1982):50-53. (Russian Original and English Abstract).
Lidbeck et al. "Lactobacilli, Anticarcinogenic Activities and Human Intestinal Microflora." *Eur. J. Cancer Prev.* 1(1992):341-353.
Lino et al. "A Study on the Effect of Bacillus Coagulans, a Spore-Forming Lactic Acid Bacteria, in Improving Microflora in the Intestine of a Human." *Prog. Med.* 17(1997):3303-3308.
Malin et al. "Promotion of IgA Immune Response in Patients with Crohn's Disease by Oral Bacteriotherapy with Lactobacillus GG." *Ann. Nutr. Metab.* 40(1996):137-145.
Marsh. "Antimicrobial Strategies in the Prevention of Dental Caries." *Caries Res.* 27(1993):72-76.
Mary El-Baz "The Essence of Herbal and Floral Teas" iUniverse;(2006)1 and 2.
Matsumara et al. "Interferon Induction by Murine Peritoneal Macrophage Stimulated with *Lactobacillus gasseri.*" *Animal Sci. Technol.* (*Jpn*). 63(1992):1157-1159.
Metchnikoff. "Longevity in the Animal Kingdom." *Prolongation of Life.* New York: The Knickerbocker Press. (1910):39-93, 132-183.
Mitchell. "Rearming in the Fight against Bacteria." *Lancet.* 352(1998):462-463.
Murphy et al. "Ciprofloxacin- and Azithromycin-Resistant *Campylobacter* Causing Travelers Diarrhea in U.S. Troops Deployed to Thailand in 1994." *Clin. Infect. Dis.* 22(1996):868-869.
Perdigon et al. "Symposium: Probiotic Bacteria for Humans: Clinical Systems for Evaluation of Effectiveness." *J. Dairy Sci.* 78(1995):1597-1606.
Perlman et al. "Persistent *Campylobacter jejuni* Infections in Patients Infected with Human Immunodeficiency Virus (HIV)." *Ann. Intern. Med.* 108(1988):540-546.
Peterson. "Clinical Aspects of *Campylobacter jejuni* Infections in Adults." *Wes. J. Med.* 161.2(1994):148-152.
Peterson. "Rheumatic Manifestations of *Campylobacter jejuni* and *C. fetus* Infections in Adults." *Scand. J. Rheumatol.* 23(1994):167-170.
Piddock. "Quinolone Resistance and *Campylobacter* spp." *J. Antimicrob. Chemother.* 36(1995):891-898.
Rafter. "The Role of Lactic Acid Bacteria in Colon Cancer Prevention." *Scand. J. Gastroenterol.* 30(1995):497-502.
Reddy et al. "Inhibitory Effect of *Bifidobacterium longum* on Colon, Mammary, and Liver Carcinogenesis Induced by 2-Amino-3-methylimidazo[4,5-f]quinoline, a Food Mutagen." *Cancer Res.* 53(1993):3914-3918.
Reid et al. "Is There a Role for Lactobacilli in Prevention of Urogenital and Intestinal Infections?" *Clin. Microbiol. Rev.* 3(1990):335-344.
Rowland et al. "Degradation of N-Nitrosamines by Intestinal Bacteria." *Appl. Microbiol.* 29(1975):7-12.
Rychen et al. "Effects of Three Microbial Probiotics on Postprandial Porto-Arterial Concentration Differences of Glucose, Galactose and Amino-Nitrogen in the Young Pig." *Brit. J. Nutr.* 74(1995):19-26.
S.D. Singh and G.P. Rao "Stevia: The Herbal Sugar of 21st Century" 2005 Sugar Technology vol. 7 No. 1 pp. 17-24.
Saavedra. "Feeding of *Bifidobacterium bifidum* and *Streptococcus thermophilus* to Infants in Hospital for Prevention of Diarrhoea and Shedding of Rotavirus." *Lancet.* 344(1994):1046-1049.
Salminen et al. "Clinical Uses of Probiotics for Stabilizing the Gut Mucosal Barrier: Successful Strains and Future Challenges." *Antonie Van Leeuwenhoek.* 70(1996):347-358.
Sawatari et al. "Development of Fermented Instant Chinese Noodle Using Lactobacillus plantarum." *Food Microbiol.* 22.6(2005):539-546.
Yamazaki et al. "Protective Effect of Bifidobacterium-Monoassociation Against Lethal Activity of *Escherichia coli.*" *Bifidobacteria Microflora.* 1(1982):55-59.
Zhang et al. "Antimutagenicity and Binding of Lactic Acid Bacteria from a Chinese Cheese to Mutagenic Pyrolyzates." *J. Dairy Sci.* 73(1990):2702-2710.

\* cited by examiner

BAKED GOODS

RELATED APPLICATIONS

This application claims the benefit of U.S.S.N. 60/966,897, filed Aug. 29, 2007, which is incorporated herein by reference in its entirety.

FIELD OF THE INVENTION

The present invention relates to the use of lactic acid-producing bacteria in baked goods.

BACKGROUND

The gastrointestinal microflora plays a number of vital roles in maintaining gastrointestinal tract function and overall physiological health. The growth and metabolism of the many individual bacterial species inhabiting the gastrointestinal tract depend primarily upon the substrates available to them, most of which are derived from the diet. (See e.g., Gibson G. R. et al., 1995. *Gastroenterology* 106: 975-982; Christl, S. U. et al., 1992. *Gut* 33: 1234-1238). These findings have led to attempts to modify the composition and metabolic activities of the bacterial community through diet, primarily with probiotics, which are live microbial food supplements.

Probiotic organisms are non-pathogenic, non-toxigenic, retain viability during storage, and survive passage through the stomach and small intestine. Since probiotics do not generally permanently colonize the host, they need to be ingested regularly for any health promoting properties to persist.

SUMMARY OF THE INVENTION

The invention describes the use of acid-producing bacteria in baked goods for human or animal consumption. Specifically, the invention provides compositions comprising a baked composition of an edible starch and an isolated *Bacillus coagulans* bacterium and methods of administering probiotic bacterial spores to a human or other animal by providing a baked good containing the spores to the human or other animal whereby the human or animal ingests the baked good and the spores germinate in the gastrointestinal tract (stomach or small intestine). Germination of spores and/or colonization of gastrointestinal tissue by the administered bacterial spores or cells is assessed by detecting the probiotic microorganism in the stool of the individual.

An exemplary baked good includes a bread, a cake, a pie, a tart, a pastry, a candy bar, an energy bar, a food bar, granola, a granola bar, a quiche, a cookie, cereal, a pizza, a corn chip, a tortilla chip, a potato chip, a baked cracker, a dehydrated vegetable, a dehydrated fruit, or a treat for companion animals. In another aspect, the baked good includes any good comprising flour. In yet another aspect, the baked good of the invention includes any good that is heated, e.g., baked (exposure of dry heat). Preferably, the baked good is a muffin. In one aspect, the baked good is a blueberry bran muffin.

Optionally, the baked composition also includes a fat. Suitable fats include oils, butters, shortenings, artificial lipids, synthetic fats, and a fat substitutes. In another aspect, the baked composition also includes a sugar, sugar substitute, or artificial sweetener.

In one aspect, the isolated *Bacillus coagulans* comprise between about 0.01% to about 50% by weight of the baked good. Optionally, the isolated *Bacillus coagulans* comprise between about 0.01% and about 10% by weight of the baked good. Preferably, the isolated *Bacillus coagulans* comprise between about 0.01% and about 0.1% by weight of the baked good.

The invention also provides bacterial species including *Bacillus coagulans*, e.g., *Bacillus coagulans* hammer, preferably *Bacillus coagulans* hammer strain Accession No. ATCC 31284, or one or more strains derived from *Bacillus coagulans* hammer strain Accession No. ATCC 31284 (e.g., ATCC Numbers: GBI-20, ATCC Designation Number PTA-6085; GBI-30, ATCC Designation Number PTA-6086; and GBI-40, ATCC Designation Number PTA-6087; see U.S. Pat. No. 6,849,256 to Farmer).

Optionally, the isolated *Bacillus coagulans* is in the form of a spore. Alternatively, the isolated *Bacillus coagulans* is in the form of a vegetative cell. In another aspect, the isolated *Bacillus coagulans* is in the form of a mixture of vegetative cells and spores.

The invention also provides for methods of making a baked good, wherein the baked good comprises a flour containing base mix and a liquid portion of water. Optionally, the method includes providing a flour containing base mix and a liquid portion of water; mixing the flour containing base mix and water to form a batter or dough; applying an isolated *Bacillus coagulans* bacterium to the batter or dough, and heat processing the batter or dough to cook the baked good. Alternatively, the method includes providing a flour containing base mix and a liquid portion of water; mixing the flour containing base mix and water to form a batter or dough; combining an isolated *Bacillus coagulans* bacterium with the batter or dough, and heat processing the batter or dough to cook the baked good.

Optionally, the isolated *Bacillus coagulans* is *Bacillus coagulans* hammer strain Accession No. ATCC 31284. In an exemplary embodiment, the isolated *Bacillus coagulans* is GBI-30 strain (ATCC Designation Number PTA-6086). In one aspect, the isolated *Bacillus coagulans* is in the form of a spore. Alternatively, the isolated *Bacillus coagulans* is in the form of a vegetative cell. In a preferred embodiment, the isolated *Bacillus coagulans* comprise between 1% and 10% by weight of the baked good.

The invention also provides compositions comprising a dry mix for baked goods including a flour and an isolated *Bacillus coagulans* bacterium.

The *Bacillus coagulans* Hammer strains of the invention are non-pathogenic and generally regarded as safe for use in human nutrition (i.e., GRAS classification) by the U.S. Federal Drug Administration (FDA) and the U.S. Department of Agriculture (USDA), and by those skilled in the art. Furthermore, the *Bacillus coagulans* Hammer strains of the invention germinate at or below human body temperature, rendering them useful as probiotics. Many *Bacillus coagulans* strains outside the Hammer group have mostly industrial applications, little or no nutritional benefit, and environmental contaminants that have not been evaluated for safety. Moreover, many other non-Hammer strains of *Bacillus coagulans* grow optimally at temperatures that exceed human body temperature and, thus, do not germinate efficiently in the human body. Such strains are less or not suitable as probiotics for human consumption.

Cited publications are incorporated herein by reference. Both the foregoing general description and the following detailed description and examples are exemplary and explanatory only and are not restrictive of the invention as claimed.

DETAILED DESCRIPTION

The present invention is directed to the discovery that non-pathogenic lactic acid-producing bacteria (i.e., "lactic acid bacteria"), such as the exemplary *Bacillus coagulans*, are useful in baked compositions as a probiotic.

Probiotic Lactic Acid-Producing Bacteria

A probiotic lactic acid-producing bacteria suitable for use in the methods and compositions of the invention produces acid and is non-pathogenic. There are many suitable bacteria identified as described herein, although the invention is not limited to currently known bacterial species insofar as the purposes and objectives of the bacteria is described. The property of acid production is important to the effectiveness of the probiotic lactic acid-producing bacteria of this invention.

The invention provides using a lactic acid-producing bacteria, such as a spore-forming *Bacillus* species, such as *B. coagulans*. Preferably, the spore-forming *Bacillus* species of the invention is *B. coagulans* Hammer.

Exemplary methods and compositions are described herein using *Bacillus coagulans* as a probiotic. Purified and/or isolated *Bacillus coagulans* is particularly useful as a probiotic in baked edible food products. Probiotic *B. coagulans* is non-pathogenic and is generally regarded as safe (i.e., GRAS classification) by the U.S. Federal Drug Administration (FDA) and the U.S. Department of Agriculture (USDA), and by those skilled in the art.

*Bacillus coagulans* is a non-pathogenic gram positive spore-forming bacteria that produces L(+) lactic acid (dextrorotatory) in fermentation conditions. It has been isolated from natural sources, such as heat-treated soil samples inoculated into nutrient medium (Bergey's Manual off Systemic Bacteriology, Vol. 2, Sneath, P. H. A., et al., eds., Williams & Wilkins, Baltimore, Md., 1986). Purified *B. coagulans* strains have served as a source of enzymes including endonucleases (e.g., U.S. Pat. No. 5,200,336); amylase (U.S. Pat. No. 4,980,180); lactase (U.S. Pat. No. 4,323,651); and cyclo-malto-dextrin glucano-transferase (U.S. Pat. No. 5,102,800). *B. coagulans* has been used to produce lactic acid (U.S. Pat. No. 5,079,164). A strain of *B. coagulans* (referred to as *L. sporogenes*; Sakaguti & Nakayama (ATCC 31284)) has been combined with other lactic acid producing bacteria and *B. natto* to produce a fermented food product from steamed soybeans (U.S. Pat. No. 4,110,477).

Bacterial species include *Bacillus coagulans*, e.g., *Bacillus coagulans* hammer, preferably *Bacillus coagulans* hammer strain Accession No. ATCC 31284, or one or more strains derived from *Bacillus coagulans* hammer strain Accession No. ATCC 31284 (e.g., ATCC Numbers: GBI-20, ATCC Designation Number PTA-6085; GBI-30, ATCC Designation Number PTA-6086; and GBI-40, ATCC Designation Number PTA-6087; see U.S. Pat. No. 6,849,256 to Farmer).

*Bacillus coagulans* was previously mis-characterized as a *Lactobacillus* and labeled as *Lactobacillus sporogenes* (See Nakamura et al. 1988. *Int. J. Syst. Bacteriol.* 38: 63-73). However, initial classification was incorrect because *Bacillus coagulans* produces spores and excretes L(+)-lactic acid through metabolism. Both of these characteristics provide key features to the utility of *Bacillus coagulans*. These developmental and metabolic aspects required that the bacterium be classified as a lactic acid *Bacillus*. In addition, it is not generally appreciated that classic Lactobacillus species are unsuitable for colonization of the gut due to their instability in the harsh (i.e., acidic) pH environment of the bile, particularly human bile. By contrast, *Bacillus coagulans* is able to survive and colonize the gastrointestinal tract in the bile environment and even grown in this low pH range.

Probiotic Activity of *Bacillus coagulans*

It is well-documented clinically that many species of bacterial, mycotic and yeast pathogens possess the ability to cause a variety of gastrointestinal disorders including, but not limited to: disruption of normal gastrointestinal biochemical function, necrosis of gastrointestinal tissues, and disruption of the bioabsorption of nutrients, and like conditions. The probiotic microorganism-containing compositions of the present invention inhibit these pathogens. Thus, the compositions of the invention are useful in the prophylactic or therapeutic treatment of conditions associated with infection by these aforementioned pathogens.

In one aspect, a *Bacillus coagulans* strain is included in the composition in the form of vegetative cells. Alternatively, the *Bacillus coagulans* strain is included in the composition in the form of spores. The invention also provides for including the *Bacillus coagulans* strain in the composition in the form of a dried cell mass, a stabilized paste, or a stabilized gel.

Because *Bacillus* spores are heat and pressure-resistant and can be stored as a dry power, they are particularly useful for formulation into and manufacture of products such as the various baked products and compositions described herein. A *Bacillus* species is well suited for the present invention, particularly species having the ability to form spores which are relatively resistant to heat and other conditions, making them ideal for storage (shelf-life) in product formulations.

The *Bacillus coagulans* of the invention survives storage (shelf-life) from about 12 days to about 2 years; from about 1 month to about 18 months; from about 3 months to about 1 year; or from about 6 months to about 9 months. For example, spores baked into a muffin remain viable and germination-competent for the self-life of the muffin (e.g., 6-12 days).

Micro-Encapsulation

In one aspect, the lactic-acid producing bacteria are incorporated into a microcapsule coating prior to addition to the baked good, using any micro-encapsulation process well-known in the art. The isolated *Bacillus coagulans* are packaged, or encapsulated, within another material in order to protect the bacteria from the surrounding environment. The capsules of the invention range in size from one-thousandth of a millimeter to seven millimeters. The internal ingredients of the microcapsule are released from their shells in various ways, including mechanical rupture of the capsule wall, dissolution of the wall, melting of the wall and diffusion through the wall. Thus, micro-encapsulation provides additional protection to the isolated *Bacillus* bacterium during heat processing (baking) of the baked goods of the invention. Physical methods of micro-encapsulation include pan coating, air-suspension coating, centrifugal extrusion, vibrational nozzle, and spray-drying. Chemical methods of micro-encapsulation include interfacial polymerization, in-situ polymerization, and matrix polymerization.

Alternatively, the lactic-acid producing bacteria is added to the baked good without micro-encapsulation.

Baked Goods

The invention is directed to the surprising discovery that lactic acid-producing bacteria, particularly *Bacillus* species, remain viable and retain their beneficial probiotic properties in heated/cooked baked goods, as the baked goods of the invention are heated to between about 300° F. to about 475° F. for about 5 minutes; about 10 minutes; about 30 minutes;

or about 1 hour. In one aspect, the baked goods of the invention are heated up to about 350° F. for about 14 minutes; about 450° F. for about 17 minutes; or about 475° F. for about 6 minutes. The preferred heat and duration will vary depending upon the particular baked good. In one aspect, muffins are heated up to about 350° F. to about 375° F. for about 14 to about 20 minutes. In another aspect, cereal is heated up to about 475° F. for about 6 minutes.

As discussed further, the compositions are formulated in many configurations because the bacterium is present as a vegetative cell or as a spore, or both, depending on the species and form of the probiotic organism. The cells/spores are present in a variety of compositions suited for use in a baked good. In one aspect, the bacterium is present as a mixture of spores and vegetative cells. Preferably, the bacterium is present as at least 90% spores, e.g., 95%, 98%, or 99% spores.

An exemplary baked good includes a bread, a cake, a pie, a tart, a pastry, a candy bar, an energy bar, granola, a granola bar, a quiche, a cookie, cereal, a food bar, a pizza, a corn chip, a tortilla chip, a potato chip, a baked cracker, a dehydrated vegetable, or a treat for companion animals. In another aspect, the baked good includes any good comprising flour. In yet another aspect, the baked good of the invention includes any good that is heated. The invention provides for baked compositions baked/cooked in an oven. The compositions described herein are baked, or dried by subjecting them to heat. Alternatively, the baked compositions are steam-heated using high heat and excessive moisture, e.g., from about 10% to about 50% w/w water/dough prior to baking. Preferably, the baked composition comprises about 30-50% w/w water/dough; about 15-30% w/w water/dough; or about 5-15% w/w water/dough prior to baking. The invention also provides for confectionary compositions such as sweets, lollipops, candy bars, chocolate, and other sweet items of snack food.

Bread consists minimally of flour and water; salt is present in most cases, and usually a leavening agent such as yeast is used; however, any well-recognized method of making bread is used in the present invention. Optionally, the flour is wheat flour, rice four, corn flour, rye flour, potato flour, millet flour, baking flour, graham flour or quinoa flour. In one aspect, the flour is self-rising or self-raising flour. In some cases, bread also contains some amounts of sugar, spices, fruit (such as raisins, pumpkins, bananas, strawberries, blueberries, and the like), vegetables (such as onion or zucchini, and the like), nuts, or seeds (such as caraway, sesame or poppy seeds). Optionally, a fat such as an oil (vegetable oil, corn oil, olive oil, grape seed oil, nut oil or fruit oil), butter, shortening, artificial lipid, synthetic fat, or a fat substitute such as olestra is also present. In yet another aspect, a sugar, sugar substitute, or artificial sweetener such as saccharin, sucralose or aspartame is present. Suitable baked goods include, but are not limited to, buns, rolls, bagels, cookies, and pastries. Preferably, the baked good is a blueberry bran muffin.

The *Bacillus* bacterium is impregnated into the baked good during the manufacturing process of the baked good (e.g., added to the batter or dough mix). The pressure and heat resistance of *Bacillus* spores makes them particularly suitable for incorporation into the baked good prior to heat processing (baking) to cook the baked good.

In one aspect, the probiotic lactic acid-producing bacteria is introduced into or onto portions of the baked good by applying a composition containing viable bacteria to the baked good during a stage of the manufacture of the baked good. Preferably, the spores and/or vegetative cells of the probiotic acid-producing bacteria are introduced into batter or dough prior to baking the baked good. Alternatively, the bacteria is added during the baking process or after the baking process has concluded.

Preferably, the *Bacillus* bacterium is introduced into the batter prior to cooking the baked good. The invention provides a batter comprising a liquid mixture, usually based on one or more flours combined with liquids, such as water, milk or beer. In one aspect, egg is included in the batter. Optionally, a leavening agent is included in the mixture to aerate and fluff-up the batter as it cooks. In one embodiment, the viscosity of batter is very "stiff" (adhering to an upturned spoon). Alternatively, the viscosity of the batter is very "thin" (similar to single cream). Preferably, heat is applied to the batter by baking, in order to cook the ingredients (thus rendering them palatable) and to "set" the batter into a solid form. Following the baking process, the baked product is suitable for immediate human or animal consumption or for freezing, i.e., to store the product for future consumption.

The invention also provides for applying the *Bacillus* bacterium to a baked good using any of a variety of known methods including, for example, applying a powder, spray-drying the probiotic onto the baked good or soaking the baked good in a solution containing the probiotic. Optionally, the *Bacillus* bacterium is applied prior to cooking the baked good. Alternatively, the *Bacillus* bacterium is applied during or after the baking process has been completed.

The invention provides for a variety of methods for placing the bacterial composition onto a baked good. However, preferred methods include a "spray-dry" method in which the baked good is exposed in a low humidity chamber to an atomized mix containing a liquid composition, where the chamber is subsequently exposed to approximately 80-110° F. to dry the liquid, thereby impregnating the material of the baked good with the components of the composition.

A typical concentration is from approximately $1 \times 10^7$ to $1 \times 10^{12}$ CFU; $1 \times 10^8$ to $1 \times 10^{11}$ CFU; or $1 \times 10^9$ to $1 \times 10^{10}$ CFU of viable bacterium or spores/in$^2$ of external surface of baked good. Following drying, the baked good is ready for immediate use, storage in a sterile package, or for freezing.

The active ingredients (i.e., live bacteria or extracellular components), comprise about 0.01% to about 50% by weight of the final composition, preferably 0.01% to 10% by weight of the final baked good. Preferably, the isolated *Bacillus coagulans* comprise between about 0.01% and about 0.1% by weight of the baked good.

In one aspect, the amount of bacteria is about $10^4$ to $10^{14}$ colony forming units (CFU) of bacteria per gram of baked good (i.e., vegetative cells and/or bacterial spores), preferably $10^5$ to $10^{13}$ CFU/g. More preferably, the concentrations are $10^8$ to $10^{13}$ CFU/g; $10^9$ to $10^{12}$ CFU/g; or $10^{10}$ to $10^{11}$ CFU/g. In one aspect, the amount of bacteria is about $1 \times 10^6$ CFU per baked good. Alternatively, the amount of bacteria is about $2 \times 10^{10}$ CFU/5 lbs of batter. The actual amount in a composition will vary depending upon the amounts of composition to be dispersed into the baked good and upon routes of dispersal.

In one aspect, the isolated *Bacillus coagulans* comprise between about 0.01% to about 10%; 0.01% to about 1%; or about 0.05% to about 0.1% by weight of the baked good. Optionally, the isolated *Bacillus coagulans* comprise about 1 mg to about 10 g; about 10 mg to about 1 g; or about 25 mg to about 75 mg by weight of the baked good.

In one aspect, the finished baked good is frozen and stored in a sterile package prior to consumption. The invention also provides for storing the baked good in a sterile package at room temperature prior to consumption. Alternatively, the baked goods are consumed immediately. In one aspect, the *Bacillus coagulans* spores survive storage (shelf-life), i.e., retain viability or the ability to germinate at physiological conditions (e.g., ingestion), from about 12 days to about 2 years; from about 1 month to about 18 months; from about 3 months to about 1 year; or from about 6 months to about 9 months. In one aspect, the *Bacillus coagulans* of the invention survives storage (shelf-life) in muffins for at least about 12 days. In another aspect, the *Bacillus coagulans* of the invention survives storage (shelf-life) in frozen pizza for at least about 2 years. In yet another aspect, the *Bacillus coagulans* of the invention survives storage (shelf-life) in food bars for at least about 6 to at least about 18 months.

EXAMPLE 1

Preparation of Bacillus Coagulans Cultures

*Bacillus coagulans* Hammer bacteria (ATCC Accession No. 31284) was inoculated and grown to a cell density of about $10^8$ to $10^9$ cells/ml in nutrient broth containing 5 g Peptone, 3 g Meat extract, 10-30 mg $MnSO_4$, and 1,000 ml distilled water, adjusted to pH 7.0, using a standard airlift fermentation vessel at 30° C. The range of $MnSO_4$ acceptable for sporulation is 1 mg/l to 1 g/l. The vegetative cells can actively reproduce up to 45° C., and the spores are stable up to 90° C. After fermentation, the *B. coagulans* bacterial cells or spores are collected using standard methods (e.g., filtration, centrifugation) and the collected cells and spores can be lyophilized, spray-dried, air-dried or frozen. As described herein, the supernatant from the cell culture is collected and used as an extracellular agent secreted by *B. coagulans*.

A typical yield from the above culture is in the range of about $10^9$ to $10^{10}$ viable spores and more typically about 100 to 150 billion cells/spores per gram before drying. Spores maintain at least 90% viability after drying when stored at room temperature for up to ten years, and thus the effective shelf life of a composition containing *B. coagulans* Hammer spores at room temperature is about 10 years.

EXAMPLE 2

Preparation of Bacillus Coagulans Spores

A culture of dried *B. coagulans* spores was prepared as follows. Ten million spores were inoculated into a one liter culture containing 24 g potato dextrose broth, 10 g of enzymic-digest of poultry and fish tissue, 5 g of FOS and 10 g MnSO4. The culture was maintained for 72 hours under a high oxygen environment at 37° C. to produce culture having about 150 billion cells per gram of culture. Thereafter, the culture was filtered to remove culture medium liquid, and the bacterial pellet was resuspended in water and freeze-dried. The freeze-dried powder is then ground to a fine powder using standard good manufacturing practice (GMP).

EXAMPLE 3

Baked Muffin with Micro-Encapsulated *Bacillus coagulans*

GBI-30, ATCC Designation Number PTA-6086, was microencapsulated (Maxx Performance; Chester, N.Y.) and added in dry powder form to blueberry bran muffin batter. The final concentration of *Bacillus coagulans* (both vegetative cells and spores) in the batter was about 20 billion ($2\times10^{10}$) CFU/5 lbs of batter (yield about 20 muffins). The final concentration of *Bacillus coagulans* (both vegetative cells and spores) in each muffin was about 1 billion ($1\times10^6$) CFU/muffin. The isolated *Bacillus coagulans* comprised about 50 mg by weight per four ounce muffin. The muffins were cooked at 350° F. for 15 minutes. Subsequently, the muffins were frozen and stored at 0° F. for 14 days. The muffins were then thawed, crushed, and the number of viable bacteria was determined. Unexpectedly, approximately 41% of the bacteria in the muffin were viable after the above-mentioned cooking and freezing cycle.

What is claimed is:

1. A chemically leavened baked muffin comprising an edible starch and isolated *Bacillus coagulans* spores, wherein said isolated *Bacillus coagulans* spores comprise GBI-30 strain (ATCC Designation No. PTA-6086) spores, wherein the *Bacillus coagulans* spores in the muffin are viable and germination-competent after baking.

2. A method of making a chemically leavened baked muffin comprising:
providing a flour containing base mix and a liquid portion of water;
mixing said flour containing base mix and said water to form a batter;
adding isolated *Bacillus coagulans* bacteria to said batter, wherein said isolated *Bacillus coagulans* bacteria comprise GBI-30 strain (ATCC Designation No. PTA-6086) bacteria, and wherein said isolated *Bacillus coagulans* bacteria comprise at least 95% spores; and
heat processing said batter to produce a baked good,
thereby making said muffin, wherein said isolated *Bacillus coagulans* bacteria in said muffin comprise at least 95% spores, and wherein the spores are viable and germination-competent after heat processing.

3. The method of claim 2, wherein said isolated *Bacillus coagulans* bacteria comprise between 1% and 10% by weight of said muffin.

4. The muffin of claim 1, further comprising a fat selected from the group consisting of oil, butter, shortening, artificial lipid, synthetic fat, and a fat substitute.

5. The muffin of claim 1, further comprising a sugar, sugar substitute, or artificial sweetener.

6. The muffin of claim 1, wherein said muffin is a blueberry bran muffin.

7. The method of claim 2, wherein said muffin is a blueberry bran muffin.

8. The muffin of claim 1, wherein said isolated *Bacillus coagulans* spores were impregnated into the muffin in an amount of about $1\times10^6$ to about $1\times10^{10}$ CFU per gram of the muffin before baking.

9. The muffin of claim 8, wherein said isolated *Bacillus coagulans* spores were impregnated into the muffin in an amount of about $1\times10^6$ to about $1\times10^8$ CFU per gram of the muffin before baking.

10. The method of claim 2, wherein said isolated *Bacillus coagulans* bacteria is added to said batter in an amount of about $1\times10^6$ to about $1\times10^8$ CFU per gram.

11. A chemically leavened baked muffin comprising an edible starch and isolated *Bacillus coagulans* spores, wherein said isolated *Bacillus coagulans* spores in the muffin are viable and germination-competent after baking.

* * * * *